United States Patent
Mohanty et al.

(10) Patent No.: US 8,092,710 B2
(45) Date of Patent: *Jan. 10, 2012

(54) HIERARCHICAL CHROMONIC STRUCTURES

(75) Inventors: Sanat Mohanty, Minneapolis, MN (US);
Hassan Sahouani, Hastings, MN (US);
Cristin E. Moran, Woodbury, MN (US)

(73) Assignee: 3M Innovative Properties Company, Saint Paul, MN (US)

(*) Notice: Subject to any disclaimer, the term of this patent is extended or adjusted under 35 U.S.C. 154(b) by 972 days.

This patent is subject to a terminal disclaimer.

(21) Appl. No.: 11/275,200

(22) Filed: Dec. 19, 2005

(65) Prior Publication Data

US 2007/0140957 A1    Jun. 21, 2007

(51) Int. Cl.
C09K 19/00 (2006.01)
C09K 19/06 (2006.01)
C09K 19/32 (2006.01)
C09K 19/52 (2006.01)

(52) U.S. Cl. ............... 252/299.01; 252/299.6; 428/1.1; 428/1.5; 430/20

(58) Field of Classification Search ............ 252/299.01, 252/299.1, 299.5–299.6; 430/20; 428/1.1, 428/1.5; 514/777, 778, 781, 782, 784, 785; 424/1.1; 264/4, 4.32; 977/778, 795; 427/213.3
See application file for complete search history.

(56) References Cited

U.S. PATENT DOCUMENTS

| | | | |
|---|---|---|---|
| 4,882,166 A | 11/1989 | Graham et al. | |
| 5,215,757 A | 6/1993 | El-Nokaly | |
| 5,827,531 A | 10/1998 | Morrison et al. | |
| 5,948,487 A | 9/1999 | Sahouani et al. | |
| 6,051,290 A | 4/2000 | Sahouani et al. | |
| 6,214,499 B1 | 4/2001 | Helber et al. | |
| 6,245,399 B1 | 6/2001 | Sahouani et al. | |
| 6,248,364 B1 | 6/2001 | Sengupta et al. | |
| 6,355,386 B1 | 3/2002 | Helber et al. | |
| 6,375,968 B1 | 4/2002 | Quong | |
| 6,395,354 B1 | 5/2002 | Sahouani et al. | |
| 6,411,354 B1 | 6/2002 | Lavrentovich et al. | |
| 6,488,866 B1 | 12/2002 | Sahouani et al. | |
| 6,527,977 B2 | 3/2003 | Helber et al. | |
| 6,538,714 B1 | 3/2003 | Sahouani et al. | |
| 6,562,363 B1 | 5/2003 | Mantelle et al. | |
| 6,570,632 B2 | 5/2003 | Lavrentovich et al. | |
| 6,574,044 B1 | 6/2003 | Sahouani et al. | |
| 6,576,712 B2 | 6/2003 | Feldstein et al. | |
| 6,645,578 B2 | 11/2003 | Sahouani et al. | |
| 6,673,398 B2 | 1/2004 | Schneider et al. | |
| 6,696,077 B2 | 2/2004 | Scherr | |
| 6,696,113 B2 | 2/2004 | Kawata et al. | |
| 6,699,533 B2 | 3/2004 | Sahouani et al. | |
| 6,777,036 B2 | 8/2004 | Bravo Vasquez et al. | |
| 6,962,734 B2 | 11/2005 | Nazarov et al. | |
| 7,601,769 B2 * | 10/2009 | Mohanty et al. | 523/206 |
| 7,629,027 B2 * | 12/2009 | Moran et al. | 427/256 |
| 7,718,716 B2 * | 5/2010 | Mohanty et al. | 523/206 |
| 2002/0066885 A1 | 6/2002 | Sahouani et al. | |
| 2002/0132065 A1 | 9/2002 | Sahouani et al. | |
| 2002/0168511 A1 | 11/2002 | Schneider et al. | |
| 2003/0008145 A1 | 1/2003 | Goldstein | |
| 2004/0058091 A1 | 3/2004 | Dutova et al. | |
| 2004/0197416 A1 | 10/2004 | Simonnet et al. | |
| 2007/0086964 A1 * | 4/2007 | Moran et al. | 424/63 |
| 2007/0086965 A1 * | 4/2007 | Mohanty et al. | 424/63 |
| 2007/0141351 A1 * | 6/2007 | Mohanty et al. | 428/411.1 |
| 2008/0063714 A1 | 3/2008 | Sahouani et al. | |

FOREIGN PATENT DOCUMENTS

| | | |
|---|---|---|
| EP | 1 232 414 B1 | 8/2002 |
| KR | 10-2003-0010846 | 2/2003 |
| WO | WO 98/37997 A2 | 9/1998 |
| WO | WO 00/22463 A1 | 4/2000 |
| WO | WO2004/033488 | 4/2004 |
| WO | WO2005/011629 | 2/2005 |
| WO | WO 2005/012488 A2 | 2/2005 |

OTHER PUBLICATIONS

Attwood et al., "Lyotropic Mesophase Formation by Anti-Asthmatic Drugs", Mol. Cryst. Liq. Cryst., (1984), pp. 349-357, vol. 108, Gordon and Breach, Science Publishers, Inc.
Kawasaki et al., "Controlled Layering of Two-Dimensional J-Aggregate of Anionic Cyanine Dye on Self-Assembled Cysteamine Monolayer on Au(111)", Langmuir, (2000), pp. 5409-5417, vol. 16, No. 12, American Chemical Society.
Lydon, "Chromonic Mesophases", Current Opinion in Colloid and Interface Science, (2004), pp. 480-490, vol. 8, Elsevier Ltd.
Lydon, "Chapter XVIII Chromonics", Handbook of Liquid Crystals, Low Molecular Weight Liquid Crystals II, (1998), pp. 981-1007, vol. 2 B, Wiley-VCH Verlag GmbH, D-60469, Weinheim.
U.S. Appl. No. 11/275,070, Tokie et al., "Method and Apparatus for Forming Chromonic Nanoparticles", filed Dec. 7, 2005.
U.S. Appl. No. 11/250,290, Moran et al., "Method for Making Chromonic Nanoparticles", filed Oct. 14, 2005.
U.S. Appl. No. 11/275,075, Ylitalo et al., "Silver Ion Releasing Articles and Methods of Manufacture", filed Dec. 8, 2005. U.S. Appl. No. 11/250,675, Mohanty et al., "Chromonic Nanoparticles Containing Bioactive Compounds", filed Oct. 14, 2005.
U.S. Appl. No. 10/996,833, Sahouani et al., "Method for Making Metallic Nanoparticles", filed Nov. 24, 2004.
U.S. Appl. No. 10/996,834, Sahouani et al., "Metallic Chromonic Compounds", filed Nov. 24, 2004.
U.S. Appl. No. 10/997,445, Sahouani et al., "Method for Making Nanostructured Surfaces", filed Nov. 24, 2004.
U.S. Appl. No. 11/284,541, Sahouani et al., "Method for Making Nanostructured Surfaces", filed Nov. 22, 2005.
U.S. Appl. No. 11/275,202, Mohanty et al., "Multilayer Chromonic Structures", filed Dec. 19, 2005.

(Continued)

Primary Examiner — Geraldina Visconti
(74) Attorney, Agent, or Firm — Gregory D. Allen (57) ABSTRACT

A method of making a chromonic structure comprises (a) preparing a first aqueous mixture comprising (i) a continuous water-soluble polymer phase and (ii) a discontinuous chromonic phase comprising a chromonic material, to form chromonic nanoparticles; (b) non-covalently crosslinking the resulting chromonic nanoparticles with a multivalent cation salt; (c) dispersing the resulting crosslinked chromonic nanoparticles in a water-soluble polymer phase to form a chromonic nanoparticle dispersion; and (d) preparing a second aqueous mixture comprising (i) the chromonic nanoparticle dispersion and (ii) a continuous chromonic phase comprising a chromonic material.

24 Claims, 1 Drawing Sheet

OTHER PUBLICATIONS

U.S. Appl. No. 11/275,364, Sahouani et al., "Encapsulated Chromonic Particles", filed Dec. 28, 2005.

Huang et al., "Nanowire Arrays Electrodeposited from Liquid Crystalline Phases", *Advanced Materials*, (Jan. 4, 2002), pp. 61-64, vol. 14, No. 1, Wiley-VCH Verlag GmbH, D-69469 Weinheim.

Aguirre, et al., "CTAB Mediated Reshaping of Metallodielectric Nanoparticles", *Nano Letters*, (2003), pp. 1707-1711, vol. 3, No. 12, American Chemical Society.

Barbic et al., "Single Crystal Silver Nanowires Prepared by the Metal Amplification Method", *Journal of Applied Physics*, (Jun. 1, 2002), pp. 9341-9345, vol. 91, No. 11, 2002 American Institute of Physics.

Brinker et al., "Review of Sol-Gel Thin Film Formation", *Journal of Non-Crystalline Solids*, (1992), pp. 424-436, vol. 147&148, Elsevier Science Publishers B. V.

Ding et al., "Structure Analysis of Nanowires and Nanobelts by Transmission Electron Microscopy", *J. Phys. Chem. B*, (2004), pp. 12280-12291, vol. 108, No. 33.

Fang et al., "Aggregation and Surface-Enhanced Raman Activity Study of Dye-Coated Mixed Silver-Gold Colloids", *Journal of Raman Spectroscopy*, (2004), pp. 914-920, vol. 35, No. 11, John Wiley & Sons, Ltd.

Hong et al., "Ultrathin Single-Crystalline Silver Nanowire Arrays Formed in an Ambient Solution Phase", *Science*, (Oct. 12, 2001), pp. 348-351, vol. 294.

Hurley, L. H. et al:, "G-quadruplexes as Targets for Drug Design", *Pharmacol Ther.*, (Mar. 2000), vol. 83, No. 3, pp. 141-158.

Kostko, A. F. et al., "Salt Effects on the Phase Behavior, Structure, and Rheology of Chromonic Liquid Crystals", *J. Phys. Chem.*, (Oct. 20, 2005), vol. 109, No. 41, pp. 19126-19133.

Kumar et al., "Linear Superclusters of Colloidal Gold Particles by Electrostatic Assembly on DNA Templates", *Advanced Materials*, (Mar. 2, 2001); pp. 341-344, vol. 13, No. 6, Wiley-VCH Verlag GmbH, D-69469 Weinheim.

Medintz et al., "Self-Assembled Nanoscale Biosensors Based on Quantum Dot FRET Donors", *Nature Materials*, (Sep. 2003), pp. 630-638, vol. 2, Nature Publishing Group.

Pardavi-Horvath et al., "Iron-Alumina Nanocomposites Prepared by Ball Milling", *IEEE Transactions on Magnetics*, (Sep. 1992), pp. 3186-3188, vol. 28, No. 5.

Stenzel et al., "The Incorporation of Metal Clusters Into Thin Organic Dye Layers as a Method for Producing Strongly Absorbing Composite Layers: An Oscillator Model Approach to Resonant Metal Cluster Absorption", *Journal of Physics D: Applied Physics*, (1995), pp. 2154-2162, vol. 28, No. 10, IOP Publishing, Ltd.

Zhang et al., "Polymer Microgels: Reactors for Semiconductor, Metal, and Magnetic Nanoparticles", *JACS*, (2004), 7908-7914, vol. 126, No. 25, American Chemical Society.

Roques et al., Encapsulation of insulin for oral administration preserves interaction of the hormone with its receptor in vitro, Apr. 1992, Diabetes, 41(4):451-456 (abstract only), http://diabetes.diabetesjournals.org/content/41/4/451.abstract.

\* cited by examiner

*Fig. 1*

HIERARCHICAL CHROMONIC STRUCTURES

FIELD

This invention relates to hierarchical chromonic structures that are useful, for example, for encapsulation and controlled release and, in another aspect, to methods for making the structures.

BACKGROUND

Encapsulation and controlled release of a substance or material may be achieved by a number of methods. Typically, a polymeric coating may be used to either surround a substance or to form a mixture with a substance. Another common approach uses macroscopic structures having openings or membranes that allow for release of a substance. Encapsulation and controlled release finds broad utility, but is particularly useful in the field of controlled release drug delivery.

PCT Publication WO 2005/012488 describes encapsulating a guest molecule (for example, a drug) in a chromonic matrix so that it can be subsequently released. The chromonic matrix can protect a drug from certain environmental conditions and then controllably deliver the drug under other environmental conditions.

SUMMARY

Briefly, the present invention provides a method of making a chromonic structure. The method comprises (a) preparing a first aqueous mixture comprising (i) a continuous water-soluble polymer phase and (ii) a discontinuous chromonic phase comprising a chromonic material, to form chromonic nanoparticles; (b) non-covalently crosslinking the resulting chromonic nanoparticles with a multivalent cation salt; (c) dispersing the resulting crosslinked chromonic nanoparticles in a water-soluble polymer phase to form a chromonic nanoparticle dispersion; and (d) preparing a second aqueous mixture comprising (i) the chromonic nanoparticle dispersion and (ii) a continuous chromonic phase comprising a chromonic material.

As used herein, "nanoparticles" refers to particles of less than about 1,000 nanometers.

As used herein, "chromonic materials" (or "chromonic compounds") refers to large, multi-ring molecules typically characterized by the presence of a hydrophobic core surrounded by various hydrophilic groups (see, for example, Attwood, T. K., and Lydon, J. E., Molec. Crystals Liq. Crystals, 108, 349 (1984)). The hydrophobic core can contain aromatic and/or non-aromatic rings. When in solution, these chromonic materials tend to aggregate into a nematic ordering characterized by a long-range order.

As used herein, "dispersion" means solid chromonic nanoparticles distributed or suspended within a liquid continuous phase that does not separate over a useful time period, for example, minutes, hours, or days.

In another aspect, this invention provides a chromonic structure comprising a continuous chromonic phase comprising polymer domains containing chromonic nanoparticles.

The present invention advantageously provides hierarchal chromonic structures. The hierarchal chromonic structures are useful in many applications.

For example, the hierarchal chromonic structures can be useful in preferential sorption applications. The continuous chromonic phase could, for example, be comprised of a chromonic material that absorbs a certain compound, while the chromonic nanoparticles are comprised of a different chromonic material that absorbs a different compound or absorbs the same compound at a different rate. Chromonic materials, for example, can be used to absorb dyes, small drug molecules, and the like.

The hierarchal chromonic structures can be particularly useful for the encapsulation and controlled release of guest compounds (for example, drugs). A drug can be encapsulated in the continuous chromonic phase or in the chromonic nanoparticles, or in both. The chromonics can protect a drug from certain environmental conditions and then controllably deliver the drug under other environmental conditions. The hierarchal structure provided by the present invention, provides increased flexibility for the controlled release of drugs.

For example, when a combination of immediate and sustained release of a drug is desired (for example, in instances where a dosage provides an initial burst of release to rapidly alleviate a particular condition, followed by a sustained delivery to provide extended treatment of the condition), the continuous chromonic phase can be formulated to provide a quick release and the chromonic nanoparticles to provide a sustained delivery.

The continuous chromonic phase can also provide increased protection from environmental conditions in comparison to the protection provided by encapsulation in a chromonic nanoparticle only. The continuous chromonic phase can, for example, protect from a different environmental condition than the chromonic nanoparticle, or it can provide an added layer of protection against the same environmental condition as the chromonic nanoparticle.

DETAILED DESCRIPTION

Any chromonic material can be useful in the methods and structures of the invention. Compounds that form chromonic phases are known in the art, and include, for example, xanthoses (for example, azo dyes and cyanine dyes) and perylenes (see, for example, Kawasaki et al., Langmuir 16, 5409 (2000), or Lydon, J., Colloid and Interface Science, 8, 480 (2004). Representative examples of useful chromonic materials include di- and mono-palladium organyls, sulfamoyl-substituted copper phthalocyanines, and hexaaryltryphenylene.

Preferred chromonic materials include those selected from one or more of the following general formulae:

(I)

-continued (II)

wherein each $R^2$ is independently selected from the group consisting of electron donating groups, electron withdrawing groups, and electron neutral groups, and $R^3$ is selected from the group consisting of a substituted and unsubstituted heteroaromatic ring, and a substituted and unsubstituted heterocyclic ring, the ring being linked to the triazine group through a nitrogen atom within the ring of $R^3$.

As depicted above, the chromonic compound is neutral, but it can exist in alternative forms such as a zwitterion or proton tautomer (for example, where a hydrogen atom is dissociated from one of the carboxyl groups and is associated with one of the nitrogen atoms in the triazine ring). The chromonic compound can also be a salt such as, for example, a carboxylate salt.

The general structures above show orientations in which the carboxyl group is para with respect to the amino linkage to the triazine backbone of the compound (formula I) and in which the carboxyl group is meta with respect to the amino linkage to the triazine backbone (formula II). The carboxyl group can also be a combination of para and meta orientations (not shown). Preferably, the orientation is para.

Preferably, each $R^2$ is hydrogen or a substituted or unsubstituted alkyl group. More preferably, $R^2$ is independently selected from the group consisting of hydrogen, unsubstituted alkyl groups, alkyl groups substituted with a hydroxy or halide functional group, and alkyl groups comprising an ether, ester, or sulfonyl. Most preferably, $R^2$ is hydrogen.

$R^3$ can be, but is not limited to, a heteroaromatic ring derived from pyridine, pyridazine, pyrimidine, pyrazine, imidazole, oxazole, isoxazole thiazole, oxadiazole, thiadiazole, pyrazole, triazole, triazine, quinoline, and isoquinoline. Preferably, $R^3$ comprises a heteroaromatic ring derived from pyridine or imidazole. A substituent for the heteroaromatic ring $R^3$ can be selected from, but is not limited to, the group consisting of substituted and unsubstituted alkyl, carboxy, amino, alkoxy, thio, cyano, amide, sulfonyl, hydroxy, halide, perfluoroalkyl, aryl, ether, and ester groups. Preferably, the substituent for $R^3$ is selected from the group consisting of alkyl, sulfonyl, carboxy, halide, perfluoroalkyl, aryl, ether, and alkyl substituted with hydroxy, sulfonyl, carboxy, halide, perfluoroalkyl, aryl, or ether. When $R^3$ is a substituted pyridine, the substituent is preferably located at the 4-position. When $R^3$ is a substituted imidazole, the substituent is preferably located at the 3-position.

Representative examples of $R^3$ include 4-(dimethylamino)pyridinium-1-yl, 3-methylimidazolium-1-yl, 4-(pyrrolidin-1-yl)pyridinium-1-yl, 4-isopropylpyridinium-1-yl, 4-[(2-hydroxyethyl)methylamino]pyridinium-1-yl, 4-(3-hydroxypropyl)pyridinium-1-yl, 4-methylpyridinium-1-yl, quinolinium-1-yl, 4-tert-butylpyridinium-1-yl, and 4-(2-sulfoethyl)pyridinium-1-yl, shown below.

$R^3$ can also be represented by the following general structure:

wherein $R^4$ is hydrogen or a substituted or unsubstituted alkyl group. More preferably, $R^4$ is selected from the group consisting of hydrogen, unsubstituted alkyl groups, and alkyl groups substituted with a hydroxy, ether, ester, sulfonate, or halide functional group. Most preferably $R^4$ is selected from the group consisting of propyl sulfonic acid, methyl, and oleyl.

$R^3$ can also be selected from heterocyclic rings such as, for example, morpholine, pyrrolidine, piperidine, and piperazine.

A preferred chromonic compound for use in the methods of the invention can be represented by one of the following formulae:

III wherein X⁻ is a counterion. Preferably, X⁻ is selected from the group consisting of $HSO_4^-$, $Cl^-$, $CH_3COO^-$, and $CF_3COO^-$.

Formula III depicts the compound in its zwitterionic form. The imidazole nitrogen therefore carries a positive charge and one of the carboxy functional groups carries a negative charge ($COO^-$).

The compound can also exist in other tautomeric forms such as where both carboxy functional groups carry a negative charge and where positive charges are carried by one of the nitrogens in the triazine groups and the nitrogen on the imidazole group.

As described in U.S. Pat. No. 5,948,487 (Sahouani et al.), which is herein incorporated by reference in its entirety, triazine derivatives with formula I can be prepared as aqueous solutions. A typical synthetic route for the triazine molecules shown in formula I above involves a two-step process. Cyanuric chloride is treated with 4-aminobenzoic acid to give 4-{[4-(4-carboxyanilino)-6-chloro -1,3,5-triazin-2-yl] amino}benzoic acid. This intermediate is treated with a substituted or unsubstituted nitrogen-containing heterocycle. The nitrogen atom of the heterocycle displaces the chlorine atom on the triazine to form the corresponding chloride salt. The zwitterionic derivative, such as that shown in formula III above, is prepared by dissolving the chloride salt in ammonium hydroxide and passing it down an anion exchange column to replace the chloride with hydroxide, followed by solvent removal. Alternative structures, such as that shown in formula II above, may be obtained by using 3-aminobenzoic acid instead of 4-aminobenzoic acid.

Chromonic materials are capable of forming a chromonic phase or assembly when dissolved in an aqueous solution (preferably, an alkaline aqueous solution). Chromonic phases or assemblies are well known in the art (see, for example, Handbook of Liquid Crystals, Volume 2B, Chapter XVIII, Chromonics, John Lydon, pp. 981-1007, 1998) and consist of stacks of flat, multi-ring aromatic molecules. The molecules consist of a hydrophobic core surrounded by hydrophilic groups. The stacking can take on a number of morphologies, but is typically characterized by a tendency to form columns created by a stack of layers. Ordered stacks of molecules are formed that grow with increasing concentration.

Preferably, the chromonic material is placed in aqueous solution in the presence of one or more pH-adjusting compounds and optionally a surfactant. The addition of pH-adjusting compounds allows the chromonic material to become more soluble in aqueous solution. Suitable pH-adjusting compounds include any known base such as, for example, ammonium hydroxide or various amines. Surfactant can be added to the aqueous solution, for example, to promote incorporation of a drug into the chromonic matrix of the chromonic nanoparticle. As used herein, "chromonic matrix" refers to chromonic materials that are aggregated into a nematic ordering.

Suitable surfactants include ionic and non-ionic surfactants (preferably, non-ionic). Optional additives such as viscosity modifiers (for example, polyethylene glycol) and/or binders (for example, low molecular weight hydrolyzed starches) can also be added.

Typically, the chromonic materials are dissolved in the aqueous solution at a temperature less than about 40° C. (more typically, at room temperature), and neutralized to pH 6-8 by the addition of a base. The neutralized chromonic material may then be combined with a solution of water-soluble polymer. One skilled in the art will recognize, however, that the geometry and size of the resulting nanoparticles can be controlled to some extent by varying the temperature.

The aqueous composition comprising a chromonic material can be mixed with a continuous phase comprising a water-soluble polymer to form the first aqueous mixture.

Preferably, the water-soluble polymer has a molecular weight of less than about 20,000. Useful water-soluble polymers include, for example, vinyl alcohol polymers, aspartic acid polymers, acrylic acid polymers, methacrylic acid polymers, acrylamide polymers, vinyl pyrrolidone polymers, poly (alkylene oxide)s, vinyl methyl ether polymers, sulfonated polyesters, complex carbohydrates, guar gum, gum arabic, gum tragacanth, larch gum, gum karaya, locust bean gum, agar, alginates, caragheenan, pectins, cellulose and cellulose derivatives, starches and modified starches, and combinations thereof. Copolymers, for example, block or random copolymers can also be useful. Preferred water-soluble polymers include, for example, cellulosics, starches (including modified starches such as phosphonated or sulfonated starches) polyvinyl alcohol, polyethylene glycol, polypropylene glycol, poly(ethylene glycol)-co-(propylene glycol), and mixtures thereof.

The particular water-soluble polymer may influence the shape of the nanoparticles. In most instances, spherical nanoparticles are obtained. In another embodiment, acicular (needle-like) metallic nanoparticles have resulted from the use of modified starch. The aspect ratios of the nanoparticles typically range from 1:4 to 1:10, and have primary dimensions from about 300 nanometers to about 10 microns. In yet another embodiment, oblate spheroidal or toroidal shapes may be obtained.

The relative concentrations of each of the components in the first aqueous mixture will vary with the desired size of the resulting nanoparticles and their intended application. Generally, however, the chromonic material will be added to the solution of water-soluble polymer in amounts sufficient such that the chromonic phase is discontinuous and the water-soluble polymer phase is continuous. The amounts of water-soluble polymer and chromonic material are generally selected so that the ratio is at least about 5:1 and less than about 99:1, and preferably 3:1 to 15:1, on a dry weight basis. Generally, the water-soluble polymer comprises from about 15 to about 25 weight percent of the aqueous mixture. Generally, the concentration of chromonic material is from about 0.25 to about 7 weight percent of the first aqueous mixture.

Optionally, surfactants and other additives (for example, short chain alcohols such as ethanol) that increase surface tension or promote coating can be added.

The chromonic nanoparticles formed from the first aqueous mixture are non-covalently crosslinked by multivalent cations. This crosslinking makes the nanoparticles insoluble in water. By non-covalent, it is meant that the crosslinking does not involve permanently formed covalent (or chemical) bonds. That is, the crosslinking does not result from a chemical reaction that leads to a new, larger molecule, but rather results from electrostatic and/or coordination associations of the cations with the host molecules that are strong enough to hold them together without undergoing a chemical reaction. These interactions are typically ionic in nature and can result from interaction of a formal negative charge on the host molecule with the formal positive charge of a multivalent cation. Since the multivalent cation has at least two positive charges, it is able to form an ionic bond with two or more chromonic molecules, that is, a crosslink between two or more chromonic molecules. Divalent and/or trivalent cations are preferred. It is more preferred that a majority of the multivalent cations are divalent. Suitable cations include any divalent or trivalent cations, with barium, calcium, magnesium, zinc, aluminum, and iron being particularly preferred.

Generally, the chromic material is crosslinked after formation of the dispersion comprising a continuous phase of water-soluble polymer and discontinuous phase of chromonic material. Typically, the dispersion is added to a solution of excess polyvalent cation salt.

Subsequent to non-covalent crosslinking, the nanoparticle surface can be modified with a surface-modifying agent to render the particles more hydrophilic, hydrophobic, biocompatible, or bioactive. The surface groups are present on the surface of the particle in an amount sufficient to provide surface-modified chromonic nanoparticles that are capable of being subsequently dispersed in a continuous phase without aggregation. The surface groups preferably are present in an amount sufficient to form a monolayer, preferably a continuous monolayer, on the surface of the chromonic nanoparticle. Generally, the crosslinked chromonic nanoparticle is first isolated from the water-soluble polymer dispersion, then re-suspended in a solution of surface modifying agent.

Surface modifying groups may be derived from surface modifying agents. Schematically, surface modifying agents can be represented by the formula A-B, where the A group is capable of attaching to the surface of the chromonic nanoparticle and the B group is a compatibilizing group that confers the desired hydrophilicity, hydrophobicity or biocompatibility. Compatibilizing groups can be selected to render the particle relatively more polar, relatively less polar or relatively non-polar.

Suitable classes of surface-modifying agents include organic oxyacids of carbon, sulfur and phosphorus, for example, alkylcarboxylates, alkyl sulfates, alkylsulfonates, alkyl phosphates and alkylphosphonates, glycoside phosphonates, and combinations thereof. The surface-modifying agents available under the trade names Tweens™ and Spans™ can also be useful.

Representative examples of polar surface-modifying agents having carboxylic acid functionality include poly(ethylene glycol) monocarboxylic acid having the chemical structure $CH_3O(CH_2CH_2O)_nCH_2COOH$ (n=2-50) and 2-(2-methoxyethoxy)acetic acid having the chemical structure $CH_3OCH_2CH_2OCH_2COOH$ in either acid or salt forms.

Representative examples of non-polar surface-modifying agents having carboxylic acid functionality include octanoic acid, dodecanoic acid and oleic acid in either acid or salt form. In the case of a carboxylic acid containing olefinic unsaturation, such as oleic acid, the carbon-carbon double bonds may be present as either the Z or E stereoisomers or as a mixture thereof.

Examples of suitable phosphorus containing acids include alkylphosphonic acids including, for example, octylphosphonic acid, decylphosphonic acid, dodecylphosphonic acid, octadecylphosphonic acid, oleylphosphonic acid and poly (ethylene glycol) monophosphonic acid having the chemical structure $CH_3O(CH_2CH_2O)_nCH_2CH_2PO_3H_2$ (n=2-50) in either acid or salt forms. In the case of a phosphonic acid containing olefinic unsaturation, such as oleylphosphonic acid, the carbon-carbon double bonds may be present as either the Z or E stereoisomers or as a mixture thereof.

Additional examples of suitable phosphorus containing acids include alkyl phosphates such as mono- and diesters of phosphoric acid including, for example, octyl phosphate, dodecyl phosphate, oleyl phosphate, dioleyl phosphate, oleyl methyl phosphate and poly(ethylene glycol) monophosphoric acid having the chemical structure $CH_3O(CH_2CH_2O)_n CH_2CH_2OPO_3H_2$ (n=2-50).

In some modifications, the B group of the surface modifying agent A-B can also contain an additional specific functional group(s) to further adjust the hydrophilicity, hydrophobicity or biocompatibility of the chromonic nanoparticle. Suitable functional groups include, but are not limited to the hydroxyl, carbonyl, ester, amide, ether, amino, and quaternary ammonium functions.

Other suitable surface modifying agents are surfactants of polymeric nature.

If biocompatibility is desired, the chromonic nanoparticles may be surface modified with glycosides phosphonates, for example, glucosides, mannosides, and galactosides of phosphonic acid.

In some embodiments, the first aqueous composition can be mixed with a noble metal salt in solution to produce metallic chromonic nanoparticles. Subsequently, the mixture can be brought into contact with a polyvalent cation salt to non-covalently crosslink the chromonic material and incorporate the noble metal salt.

Preferred noble metal salts include silver salts (for example, silver nitrate, silver acetate, and the like), gold salts (for example, gold sodium thiomalate, gold chloride, and the like), platinum salts (for example, platinum nitrate, platinum chloride, and the like), and mixtures thereof. Other transition metals can also be used. In particular, salts of monovalent transition metal cations can be used.

The metal salt can be reduced to produce a suspension of elemental noble metal nanoparticles contained in the crosslinked chromonic nanoparticle. This can be accomplished via reduction methods known in the art. For example, the reduction can be accomplished by using a reducing agent (for example, tris(dimethylamino)borane, sodium borohydride, potassium borohydride, or ammonium borohydride), electron beam (e-beam) processing, or ultraviolet (UV) light.

The metal nanoparticles can, for example, serve as a tag. They can be useful in numerous applications such as medical imaging, optical switching devices, optical communication systems, infrared detectors, infrared cloaking devices, chemical sensors, passive solar radiation collection or deflecting devices and the like.

The crosslinked chromonic nanoparticles formed from the first aqueous mixture can be dispersed in a water-soluble polymer phase. A second aqueous mixture comprising the dispersion and a continuous chromonic phase comprising a chromonic material can then be prepared.

Any of the chromonic materials described above can be used in the continuous chromonic phase of the second aqueous mixture. The chromonic material used in the second aqueous mixture can be the same chromonic material or a different chromonic material than that utilized in the first aqueous mixture. For example, in some applications it can be advantageous to use two different chromonic materials that have different absorbencies or different stabilities in low pH conditions.

Any of the water-soluble polymers described above can be used for the water-soluble polymer phase of the chromonic nanoparticle dispersion. The water-soluble polymer used in the chromonic nanoparticle dispersion can be the same water-soluble polymer or a different water-soluble polymer than that utilized in the first aqueous mixture.

The second aqueous mixture can be made using essentially the same procedure as described for making the first aqueous mixture, except that concentrations of the components will vary.

For the second aqueous mixture, the chromonic material can be dissolved in an aqueous solution. Generally, the chromonic material will be added to the solution to achieve a concentration in the range of about 4 to about 30 (preferably, about 4 to about 20) percent by weight of the solution. This aqueous solution comprising a chromonic material can then be mixed with the chromonic nanoparticle dispersion. Typically, the amount of water-soluble polymer and chromonic material are selected so that the ratio is at least about 0.01:1 and less than about 1:1 (preferably less than 0.2:1) on a dry weight basis.

The continuous chromonic phase can also comprise a non-ionic surfactant. Preferably, the non-ionic surfactant is an alkyl glucoside surfactant. The weight ratio of non-ionic surfactant to chromonic material can generally be at least about 0.01:1 and less than about 0.3:1 (preferably less than about 0.03:1).

Optionally, other additives (for example, short chain alcohols such as ethanol) that increase surface tension or promote coating can be added. The second aqueous composition can optionally be mixed with a noble metal salt in solution. The metal salt can then be reduced to produce a suspension of elemental noble metal nanoparticles contained in the continuous chromonic phase.

The resulting mixture can be applied to the surface of a substrate. Suitable substrates include any solid materials that will accept the application of the mixture (for example, glass or polymeric films).

The mixture can be applied by any useful means that provides for the ordered arrangement of the chromonic materials such as, for example, by coating techniques such as wire-wound coating rod or extrusion die methods. Preferably, shear orientation or magnetic orientation is applied to the mixture either during or after application. The application of shear or magnetic force to the mixture can help promote alignment of the chromonic materials such that, upon drying, an oriented structure or matrix is obtained. The continuous chromonic phase will comprise polymer domains. The polymer domains can be spherical, oblate spheroidal, columnar, or lamellar in shape, and typically range in size from the nanometer scale to the millimeter scale. For example, in some embodiments, the polymer domains can have primary dimensions between about 500 nanometers and about 5 millimeters. The polymer domain shape and size can be influenced by the nature of the polymer used, by the concentration of the polymer, and/or by additives. The chromonic nanoparticles are contained within the polymer domains.

Drying of the coated layer can be achieved using any means suitable for drying aqueous coatings. Useful drying methods will not damage the coating or significantly disrupt the orientation of the coated layer imparted during coating or application.

Optionally, the resulting chromonic surface (that is, the continuous chromonic phase) can be non-covalently crosslinked by multivalent cations. Generally, the chromic material is crosslinked after formation of the dispersion comprising a discontinuous water-soluble polymer phase and a continuous chromonic phase comprising chromonic material. Typically, the dispersion is added to a solution of excess polyvalent cation salt.

Subsequent to non-covalent crosslinking, the continuous chromonic phase can be contacted with a surface-modifying agent, as described above, to render the matrix more hydrophilic, hydrophobic, biocompatible, or bioactive.

In some embodiments, the present invention can be used for the encapsulation and controlled release of one or more guest compounds. The present invention provides a continuous chromonic phase comprising water-soluble polymer domains containing chromonic nanoparticles. Guest compounds can be encapsulated within the chromonic nanoparticles and/or within the continuous chromonic phase. When guest compounds are encapsulated in both the chromonic nanoparticles and in the continuous chromonic phase, they may be the same guest compound or different guest compounds. More than one type of guest compound can also be encapsulated within the chromonic nanoparticles and/or within the continuous chromonic phase. In addition, chromonic nanoparticles containing differing guest compounds can be contained in the polymer domains (that is, chromonic nanoparticles containing a first encapsulated guest compound and chromonic nanoparticles comprising a second encapsulated guest compound can be contained within the polymer domains).

For example, a guest molecule that is ordinarily soluble in water may be prevented from dissolving into water, since it is encapsulated within a water-insoluble chromonic nanoparticle or continuous chromonic phase. Likewise, the chromonic nanoparticle or continuous chromonic phase may effectively isolate guest molecules that are unstable in the presence of an acid. Thus, they will not degrade while encapsulated within the nanoparticle or matrix. The chromonic nanoparticle or continuous chromonic phase can also be used to separate reactants to prevent them from reacting.

Examples of useful guest compounds include dyes, cosmetic agents, fragrances, flavoring agents, and bioactive compounds, such as drugs, herbicides, pesticides, pheromones, and antimicrobial agents (for example, antibacterial agents, antifungal agents, and the like). A bioactive compound is herein defined as a compound intended for use in the diagnosis, cure, mitigation, treatment or prevention of disease, or to affect the structure or function of a living organism. Drugs (that is, pharmaceutically active ingredients) that are intended to have a therapeutic effect on an organism are particularly useful guest compounds. Alternatively, herbicides and pesticides are examples of bioactive compounds intended to have a negative effect on a living organism, such as a plant or pest. Although any type of drug can be employed in the present invention, particularly suitable drugs include those that are relatively unstable when formulated as solid dosage forms, those that are adversely affected by the low pH conditions of the stomach, those that are adversely affected by exposure to enzymes in the gastrointestinal tract, and those that are desirable to provide to a patient via sustained or controlled release.

The continuous chromonic phase and the chromonic nanoparticle will selectively protect a drug from certain environmental conditions and then controllably deliver the drug under other environmental conditions. For example, chromonic materials can be stable in the acidic environment of the stomach and will dissolve when passed into the non-acidic environment of the intestine when administered to an animal as a result of the change in pH. Chromonic materials can also protect a drug from enzymatic degradation.

The present invention can also be used to effectively isolate drug molecules in a particle, such that unfavorable interactions (for example, chemical reactions) between different drugs in a combination dosage form, unfavorable changes in a single drug component (for example, Ostwald ripening or particle growth, changes in crystalline form), and/or unfavorable interactions between a drug and one or more excipients can be avoided. For example, the present invention allows two drugs (or chemical reactants) that are ordinarily unstable in each other's presence to be formulated into stable dosage form by encapsulating them both in chromonic nanoparticles, or by encapsulating one in chromonic nanoparticles and the other in the continuous chromonic phase.

Guest compounds can be contained or intercalated in chromonic nanoparticles by adding guest compounds to the first aqueous solution of chromonic material. Alternatively, a guest compound can be dispersed or dissolved in another excipient or vehicle, such as an oil or propellant, prior to mixing with the chromonic materials or multivalent cation solutions. Nanoparticles can be collected by, for example, filtration, spraying, or other means, and dried to remove the aqueous carrier.

A guest compound, such as a drug, can be dissolved in an aqueous dispersant-containing solution prior to introduction of the chromonic material. Suitable dispersants include alkyl phosphates, phosphonates, sulfonates, sulfates, or carboxylates, including long chain saturated fatty acids or alcohols and mono or poly-unsaturated fatty acids or alcohols. Oleyl phosphonic acid is an example of a suitable dispersant. Although not to be bound by any particular theory, it is thought that the dispersant aids in dispersing the guest compound so that it may be better encapsulated.

An alkaline compound can be added to the guest compound solution prior to introduction of the chromonic material. Alternatively, an alkaline compound can be added to a chromonic material solution prior to mixing the guest compound and chromonic material solutions. Examples of suitable alkaline compounds include ethanolamine, sodium or lithium hydroxide, or amines such as mono, di, triamines or polyamines. Although not to be bound by theory, it is thought that alkaline compounds aid in dissolving the host compound, particularly where the host compound is a triazine compound such as those described in formulas I and II above.

Although large particles (for example, on the order of several millimeters in diameter) may be prepared, the mass median diameter of particles of the present invention is typically less than 1000 nanometers in size, usually less than 500 nanometers in size, and in some cases less than 100 nanometers in size. In certain instances it may be desired to have particles greater than 1 µm in size. In particular, these particle sizes may be desirable for oral delivery of drugs that are unstable in the intestine due to the presence of certain enzymes. Examples of such drugs include proteins, peptides, antibodies, and other biologic molecules that may be particularly sensitive to the body's enzymatic processes. In such cases, these small particles may be taken up into the intestinal wall directly, such that the particle primarily dissolves after passing the intestinal barrier, so that the amount of the sensitive drug exposed to the intestinal environment is minimized.

Guest compounds can be contained or intercalated in the continuous chromonic phase by adding guest compounds to either the second aqueous solution of chromonic material or, if the continuous chromonic phase is non-covalently crosslinked, the multivalent cation solution prior to precipitation. As described above, a guest compound can be dispersed or dissolved in another excipient or vehicle, such as an oil or propellant, prior to mixing with the chromonic materials or multivalent cation solutions.

The chromonic nanoparticles and continuous chromonic phase are dissolvable in an aqueous solution of univalent cations or other non-ionic compounds such as surfactants. Typical univalent cations include sodium and potassium. The concentration of univalent cations needed to dissolve the chromonic nanoparticles and continuous chromonic phase will depend on the type and amount of the chromonic molecules within the nanoparticles and matrix. Therefore, different chromonic materials can be chosen for the nanoparticles and the continuous phase so that they dissolve at different concentrations. Generally, however, for complete dissolution there should be at least a molar amount of univalent cations equivalent to the molar amount of carboxyl groups in the matrix. In this way, there will be at least one univalent cation to associate with each carboxyl group.

The rate at which a chromonic nanoparticle or continuous chromonic phase dissolves can be adjusted by adjusting the type and amount of multivalent cation used for crosslinking. In the case where a quick release of guest compound within the continuous chromonic phase is desired, the continuous chromonic phase may not be crosslinked.

Although divalent cations will be sufficient to crosslink the chromonic nanoparticles and the continuous chromonic phase, higher valency cations will provide additional crosslinking and lead to slower dissolution rates. In addition to valency, dissolution rate will also depend on the particular cation type. Therefore, different valency and/or cation types can be chosen for the nanoparticles and the continuous phase so that they dissolve at different rates. For example, a weakly coordinating divalent cation, such as magnesium, will generally lead to faster dissolution than a strongly coordinating divalent cation, such as calcium or zinc, which has an empty electron orbital capable of forming a coordination bond with a free electron pair.

Different cation types can be mixed so as to give an average cation valency that is not an integer. In particular, a mixture of divalent and trivalent cations will generally cause a slower dissolution rate than where all of the cations are divalent. In one aspect, all of the guest compound will be released over time, but it may be desired in certain applications to have only a portion of the guest compound be released. For instance, the type or amount of chromonic material and multivalent cation can be adjusted such that the total amount of guest compound that is released will vary depending on the environment into which they are placed. In one embodiment, the chromonic nanoparticle (or continuous chromonic phase) will not dissolve in an acidic solution, thus protecting acid sensitive guest compounds from degradation. In another, the chronic nanoparticle (or continuous chromonic phase) will not dissolve in an acidic solution containing univalent cations, thus protecting acid sensitive guest compounds from degradation.

In the particular instance where the guest compound is a drug, two common types of general release profiles that are desired are immediate or sustained. For immediate release use it is typically desired that most of the drug will be released in a time period of less than about 4 hours, generally less than about 1 hour, often less than about 30 minutes, and in some cases less than about 10 minutes. In some instances it will desired that drug release will be nearly instantaneous, that is it will take place in a matter of seconds. For sustained (or controlled) release uses it is typically desired that most of the drug will be released over a time period greater than or equal to about 4 hours. Periods of one month or more may be desired, for example in various implantable applications. Oral sustained release dosages will generally release most of the drug over a time period of about 4 hours to about 14 days, sometimes about 12 hours to about 7 days. In one aspect it may be desired to release most of the drug over a time period of about 24 to about 48 hours.

A combination of immediate and sustained may also be desired, for example, in instances where a dosage provides an initial burst of release to rapidly alleviate a particular condition, followed by a sustained delivery to provide extended treatment of the condition. In such instances, the continuous chromonic phase can be formulated to provide a quick release and the chromonic nanoparticles to provide a sustained delivery.

In some instances it may be desirable to have a pulsatile or multi-modal release of drug, such that the rate of release varies over time, for instance increasing and decreasing to match the circadian rhythm of an organism. Likewise, it may be desirable to provide a delayed release of drug, such that a dosage may be administered at a convenient time, such as just before going to sleep, but prevent release of the drug until a later time when it may be more efficacious, such as just before waking. One approach for achieving pulsatile, multi-modal, or delayed release profiles may be to mix two or more types of nanoparticles having different drug release characteristics. Alternatively, the particles and the continuous phase may be formed having different drug release characteristics.

The present invention is particularly useful for encapsulating drugs for used in oral dosage delivery. Typical oral dosage forms include solid dosages, such as tablets and capsules, but can also include other dosages administered orally, such as liquid suspensions and syrups. The continuous chromonic phase and/or chromonic nanoparticles of the invention can be stable in the acidic environment of the stomach and will dissolve when passed into the non-acidic environment of the intestine when administered to an animal. When the continuous chromonic phase and/or nanoparticles are stable in acidic solution, the particles can generally be stable for periods of time longer than 1 hour, sometimes longer than 12 hours, and may even be stable for more than 24 hours when present in an acidic environment with a pH less than 7.0 (for example, less than about 5.0), and in some cases less than about 3.0.

EXAMPLES

Objects and advantages of this invention are further illustrated by the following examples, but the particular materials and amounts thereof recited in these examples, as well as other conditions and details, should not be construed to unduly limit this invention.

Unless otherwise noted, all reagents and compounds were or can be obtained from Sigma-Aldrich Chemical Co., St. Louis, Mo. As used herein, "purified water" refers to water available under the trade designation "OMNISOLVE" from EMD Chemicals, Inc., Gibbstown, N.J.

The sonicator used was the Ultrasonic Processor Model VCX-13 with a 6 mm microtip, available from Sonics and Materials of Newtown, Conn. The optical microscope used was microscope Model UCT with FC6 cyro attachment available from Leica Microsystems, Inc., Bannockburn, Ill.) and measurements using dynamic light scattering techniques were made on a Malvern Zen 3600 from Malvern Company, Worcestershire, UK.

Preparation of the Chromonic Mixture (Chromonic Mixture)

A mixture containing the chromonic compound of Formula IV (30% by weight) in purified water was magnetically stirred in a flask for approximately 45 minutes to make a white paste. A freshly prepared solution of Sodium hydroxide (50% by weight in purified water) was added drop wise to the flask containing the white paste until its appearance changed to a creamy liquid crystalline solution. The pH of this mixture was maintained to be at or less than 7.5 during this addition process by controlling the addition of sodium hydroxide solution. The resulting creamy liquid crystalline solution was used as needed.

Preparation of Fluorescent Bovine Serum Albumin solution (fBSA)

Purified water (5 ml) was added to Fluorescein isothiocyanate conjugate albumin (fBSA, 250 mg) and then magnetically stirred for 15 minutes to make a solution of 50 mg fBSA/ml solution. This solution was used as needed.

Example 1

Chromonic mixture—fBSA solution was prepared by mixing fBSA (3 ml) with the chromonic mixture (10 ml) for 15 minutes to provide a solution of chromonic mixture—fBSA (13 ml) containing about 23% chromonic mixture and 50 mg fBSA/g of chromonic compound of Formula IV. This solution was used as needed.

A portion of the chromonic mixture—fBSA was dispersed in a solution containing hydroxypropyl methylcellulose (HPMC, 25% in purified water; chromonic mixture to HMPC solution ratio 1:20 by weight) by stirring for 30 minutes at room temperature.

This emulsion (0.6 g) was then added to an aqueous solution (10 ml) containing calcium chloride and zinc chloride (5% each). This solution was shaken for 30 minutes at room temperature and centrifuged at 3500 rpm for 20 minutes. The resulting supernatant was then discarded. The remaining residue was washed with purified water (10 ml) and was centrifuged again at 3500 rpm for 20 minutes. A sample of the resulting residue fluoresced green when viewed under an optical microscope and measurements using dynamic light scattering techniques indicated it to contain particles in the range of 500 nm.

Figure 1:
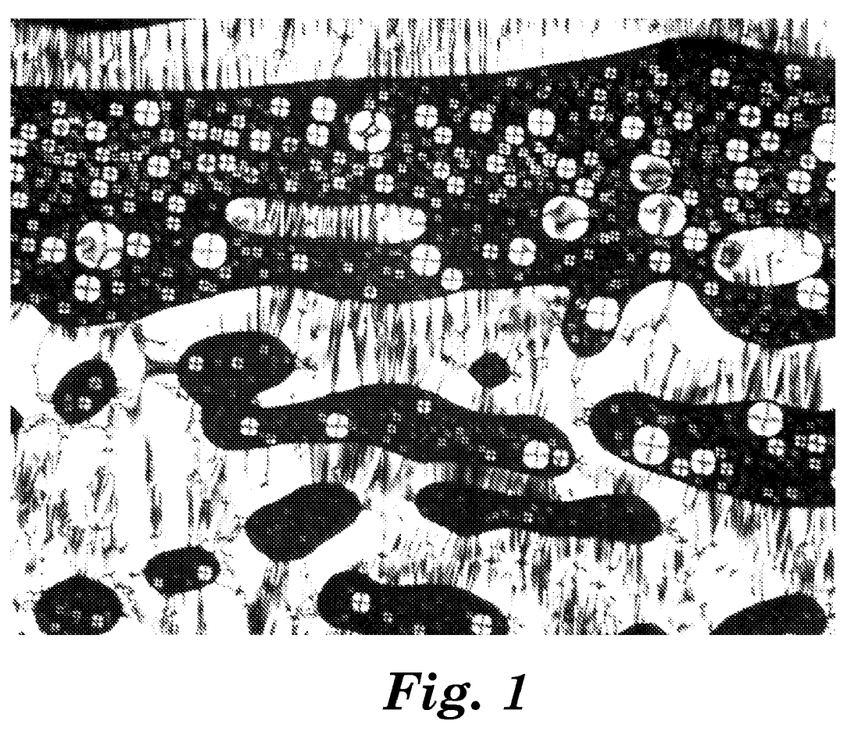
FIG. 1 is an optical microscope image of a chromonic structure of the invention as described in Example 1.

The residue sample isolated after the washing step (0.6 g) was dispersed in a solution containing HPMC (2.0 ml, 25% in purified water) by first sonicating for 30 seconds and then by stirring for 20 minutes at room temperature. This emulsion was then added to the chromonic mixture (10 ml) and the contents were mixed for an additional 30 min. A sample of this resulting mixture, when observed using an optical microscope, indicated the presence of yellow (fBSA) and blue (zinc chloride) fluorescent particles in the dark HPMC domains surrounded by the second chromonic mixture. No yellow fluorescence was observed in the dispersed chromonic mixture. FIG. 1 is an optical microscope image of the sample viewed in reflected brightfield mode through a polarizer at 100x magnification. The maltese crosses on the particles indicate that they are birefringent. The image shows that the particles are dispersed in polymer domains (dark regions). The polymer domains are contained within a chromonics matrix.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:
1. A method of making a chromonic structure comprising:
  (a) preparing a first aqueous mixture comprising (i) a continuous water-soluble polymer phase and (ii) a discontinuous chromonic phase comprising a chromonic material, to form chromonic nanoparticles;
  (b) non-covalently crosslinking the resulting chromonic nanoparticles with a multivalent cation salt;

(c) dispersing the resulting crosslinked chromonic nanoparticles in a water-soluble polymer phase to form a chromonic nanoparticle dispersion; and (d) preparing a second aqueous mixture comprising (i) the chromonic nanoparticle dispersion and (ii) a continuous chromonic phase comprising a chromonic material.

2. The method of claim 1 wherein the discontinuous chromonic phase or the continuous chromonic phase further comprises a guest compound.

3. The method of claim 2 wherein the guest compound is a bioactive compound.

4. The method of claim 3 wherein the bioactive compound is selected from the group consisting of drugs, herbicides, pesticides, pheromones, and antimicrobial agents.

5. The method of claim 4 wherein the bioactive compound is a drug.

6. The method of claim 2 wherein the discontinuous chromonic phase comprises a guest compound.

7. The method of claim 6 further comprising:
preparing a third aqueous mixture comprising (i) a continuous water-soluble polymer phase and (ii) a discontinuous chromonic phase comprising a chromonic material and a second guest compound, to form chromonic nanoparticles comprising the second guest compound;
non-covalently crosslinking the resulting chromonic nanoparticles comprising the second guest compound with a multivalent cation salt; and
dispersing the resulting crosslinked chromonic nanoparticles comprising the second guest compound in the water-soluble polymer phase of step (c).

8. The method of claim 1 wherein the continuous chromonic phase comprises a guest compound.

9. The method of claim 1 wherein the discontinuous chromonic phase and the continuous chromonic phase each comprise an independently selected guest compound.

10. The method of claim 9 wherein the discontinuous chromonic phase guest compound is reactive with the continuous chromonic phase guest compound.

11. The method of claim 9 wherein at least one of the guest compounds is a bioactive compound.

12. The method of claim 11 wherein at least one of the guest compounds is selected from the group consisting of drugs, herbicides, pesticides, pheromones, and antimicrobial agents.

13. The method of claim 12 wherein at least one of the guest compounds is a drug.

14. The method of claim 1 wherein the continuous chromonic phase further comprises a non-ionic surfactant.

15. The method of claim 1 further comprising non-covalently crosslinking the continuous chromic phase.

16. The method of claim 1 wherein the multivalent cation of the multivalent cation salt is selected from the group consisting of $Ba^{2+}$, $Ca^{2+}$, $Fe^{2+}$, $Fe^{3+}$, $Zn^{2+}$, $Mg^{2+}$, and $Al^{3+}$.

17. The method of claim 1 wherein the water-soluble polymer of the first aqueous mixture and the water-soluble polymer of the chromonic nanoparticle dispersion of step (c) are independently selected from the group consisting of vinyl alcohol polymers, aspartic acid polymers, acrylic acid polymers, methacrylic acid polymers, acrylamide polymers, vinyl pyrrolidone polymers, poly(alkylene oxide)s, vinyl methyl ether polymers, sulfonated polyesters, complex carbohydrates, guar gum, gum arabic, gum tragacanth, larch gum, gum karaya, locust bean gum, agar, alginates, caragheenan, pectins, cellulose and cellulose derivatives, starches and modified starches, and combinations thereof.

18. The method of claim 1 wherein the chromonic material of the first aqueous mixture and the chromonic material of the second aqueous mixture are independently selected from one or more of the following general formulae:

wherein
each $R^2$ is independently selected from the group consisting of electron donating groups, electron withdrawing groups, and electron neutral groups, and
$R^3$ is selected from the group consisting of substituted and unsubstituted heteroaromatic rings and substituted and unsubstituted heterocyclic rings, said rings being linked to the triazine group through a nitrogen atom within the ring of $R^3$,
and zwitterions, proton tautomers, and salts thereof.

19. The method of claim 18 wherein the chromonic material of the first aqueous mixture and the chromonic material Of the second aqueous mixture arc independently selected from one or more of the following general formulae:

wherein X" is a counterion.

20. The method of claim 1 wherein the first aqueous mixture further comprises a noble metal salt.

21. The method of claim 20 further comprising reducing the noble metal salt to produce a suspension of elemental noble metal nanoparticles contained in the crosslinked chromonic nanoparticle.

22. The method of claim 1 wherein the second aqueous mixture further comprises a noble metal salt.

23. The method of claim 22 further comprising reducing the noble metal salt to produce a suspension of elemental noble metal nanoparticles contained in a continuous chromonic phase matrix.

24. The method of claim 1 further comprising:
(e) drying the second aqueous mixture such that the continuous chromonic phase comprises domains of the chromonic nanonparticle dispersion.

* * * * *

UNITED STATES PATENT AND TRADEMARK OFFICE
CERTIFICATE OF CORRECTION

| | | |
|---|---|---|
| PATENT NO. | : 8,092,710 B2 | Page 1 of 1 |
| APPLICATION NO. | : 11/275200 | |
| DATED | : January 10, 2012 | |
| INVENTOR(S) | : Sanat Mohanty | |

It is certified that error appears in the above-identified patent and that said Letters Patent is hereby corrected as shown below:

Column 2
Line 46-47, delete "xanthoses" and insert -- xanthosis --, therefor.

Line 52-53, delete "hexaaryltryphenylene." and insert -- hexaaryltriphenylene. --, therefor.

Column 6
Line 25, delete "caragheenan," and insert -- carrageenan, --, therefor.

Column 14
Line 46, delete "1OOx" and insert -- 100x --, therefor.

Column 15
Line 55, in Claim 16, delete "$Fe^{2+},Fe^{3+},$" and insert -- $Fe^{2+}$, $Fe^{3+}$, --, therefor.

Line 65, in Claim 17, delete "caragheenan," and insert -- carrageenan, --, therefor.

Column 16
Line 36, in Claim 19, delete "Of" and insert -- of --, therefor.

Line 36, in Claim 19, delete "arc" and insert -- are --, therefor.

Line 61, in Claim 19, delete "X"" and insert -- X⁻ --, therefor.

Column 18
Line 4, in Claim 24, delete "nanonparticle" and insert -- nanoparticle --, therefor.

Signed and Sealed this
Tenth Day of April, 2012

David J. Kappos
*Director of the United States Patent and Trademark Office*